US008263681B2

(12) United States Patent
Craig et al.

(10) Patent No.: US 8,263,681 B2
(45) Date of Patent: *Sep. 11, 2012

(54) DENTAL COMPOSITIONS WITH NATURAL TOOTH FLUORESCENCE

(75) Inventors: Bradley D. Craig, Cottage Grove, MN (US); Gregory A. Kobussen, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 269 days.

This patent is subject to a terminal disclaimer.

(21) Appl. No.: 12/520,402

(22) PCT Filed: Dec. 21, 2007

(86) PCT No.: PCT/US2007/088528
§ 371 (c)(1),
(2), (4) Date: Jun. 19, 2009

(87) PCT Pub. No.: WO2008/083067
PCT Pub. Date: Jul. 10, 2008

(65) Prior Publication Data
US 2010/0016464 A1    Jan. 21, 2010

Related U.S. Application Data

(60) Provisional application No. 60/877,513, filed on Dec. 28, 2006.

(51) Int. Cl.
*A61K 6/02* (2006.01)
*A61K 6/083* (2006.01)
*C08J 3/28* (2006.01)
*C08F 2/50* (2006.01)
*C08F 2/42* (2006.01)

(52) U.S. Cl. ........ 523/115; 523/105; 523/109; 523/112; 523/113; 523/114; 523/111; 523/116; 523/117; 523/118; 523/120; 522/74; 522/71; 522/80; 522/908; 522/113; 522/114; 522/90; 522/96; 522/100; 522/103; 522/81; 522/83; 522/150; 522/151; 522/152; 522/153; 522/154; 522/168; 522/170

(58) Field of Classification Search ............ 523/105, 523/109, 112, 113, 114, 115, 111, 116, 117, 523/118, 120; 522/71, 74, 80, 908
See application file for complete search history.

(56) References Cited

U.S. PATENT DOCUMENTS

| | | |
|---|---|---|
| 2,481,344 A | 9/1949 | Reimert |
| 2,831,862 A | 4/1958 | Biel |
| 3,018,262 A | 1/1962 | Schroeder |
| 3,117,099 A | 1/1964 | Proops |
| 3,344,115 A | 9/1967 | Rein |
| 3,452,437 A | 7/1969 | Chang |
| 4,158,641 A | 6/1979 | Miyai |
| 4,198,244 A | 4/1980 | Binns |
| 4,259,075 A | 3/1981 | Yamauchi |
| 4,298,738 A | 11/1981 | Lechtken |
| 4,324,744 A | 4/1982 | Lechtken |
| 4,335,250 A | 6/1982 | Umezawa |
| 4,356,296 A | 10/1982 | Griffith |
| 4,385,109 A | 5/1983 | Lechtken |
| 4,499,251 A | 2/1985 | Omura |
| 4,503,169 A | 3/1985 | Randklev |
| 4,537,940 A | 8/1985 | Omura |
| 4,539,382 A | 9/1985 | Omura |
| 4,600,389 A | 7/1986 | Schwartz |
| 4,629,746 A | 12/1986 | Michl |
| 4,642,126 A | 2/1987 | Zador |
| 4,645,455 A | 2/1987 | Kosmos |
| 4,648,843 A | 3/1987 | Mitra |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,737,593 A | 4/1988 | Ellrich |
| 4,752,338 A | 6/1988 | Reiners |
| 4,767,798 A | 8/1988 | Gasser |
| 4,872,936 A | 10/1989 | Engelbrecht |
| 4,882,365 A | 11/1989 | Gasser |
| 5,026,902 A | 6/1991 | Fock |
| 5,076,844 A | 12/1991 | Fock |
| 5,102,461 A * | 4/1992 | Rheinberger et al. ........... 106/35 |
| 5,130,347 A | 7/1992 | Mitra |
| 5,154,762 A | 10/1992 | Mitra |
| 5,211,748 A | 5/1993 | Robinson |

(Continued)

FOREIGN PATENT DOCUMENTS

DE    19646037    5/1998

(Continued)

OTHER PUBLICATIONS

Adamson, "Aminoalkyl Tertiary Carbinols and Derived Products. Part I. 3-Amino-1 : 1-Diphenylpropan-1-Ols.", Journal of the Chemical Society, 1949, Part V, pp. S144-S155. [Month unknown but believed to be prior to the date of the filing of the present application.]
Adelman, "The Reactions of Vinyl Acetate with Aliphatic Hydroxy Compounds. A New Synthesis of Vinyl Ethers", J. Am. Chem. Soc., 1953, vol. 75, pp. 2678-2682.
Berlman, "Handbook of Fluorescence Spectra of Aromatic Molecules", New York, Academic Press (1971).
CIE Technical Report, "Colorimetry", CIE 15:2004, Third Ed. (ISBN 3901906339).
Crivello, "Anthracene electron-transfer photosensitizers for onium salt induced cationic photopolymerizations", Journal of Photochemistry and Photobiology A: Chemistry, 2003, vol. 159, pp. 173-188. XP002325847.

(Continued)

*Primary Examiner* — Sanza McClendon
(74) *Attorney, Agent, or Firm* — Julie A. Lapos-Kuchar; Dean A. Ersfeld

(57) ABSTRACT

The invention features a dental composition containing a polycyclic aromatic compound, such as 2-ethyl 9,10-dimethoxy anthracene (EDMOA), in an amount that provides the composition with fluorescence mimicking that of natural teeth.

19 Claims, No Drawings

U.S. PATENT DOCUMENTS

| | | | |
|---|---|---|---|
| 5,269,682 A | 12/1993 | Kesling |
| 5,501,727 A | 3/1996 | Wang |
| 5,530,038 A | 6/1996 | Yamamoto |
| 5,545,676 A | 8/1996 | Palazzotto |
| 6,022,819 A | 2/2000 | Panzera |
| 6,030,606 A | 2/2000 | Holmes |
| 6,031,015 A | 2/2000 | Ritter |
| 6,043,361 A | 3/2000 | Evans |
| 6,187,833 B1 | 2/2001 | Oxman |
| 6,251,963 B1 | 6/2001 | Köhler |
| 6,262,142 B1 | 7/2001 | Wang |
| 6,306,926 B1 | 10/2001 | Bretscher |
| 6,344,556 B1 | 2/2002 | Evans |
| 6,387,981 B1 | 5/2002 | Zhang |
| 6,391,281 B1 | 5/2002 | Rueggeberg |
| 6,458,868 B1 | 10/2002 | Okada |
| 6,495,643 B1 | 12/2002 | Evans |
| 6,566,413 B1 | 5/2003 | Weinmann |
| 6,572,693 B1 | 6/2003 | Wu |
| 6,624,236 B1 | 9/2003 | Bissinger |
| 6,730,156 B1 | 5/2004 | Windisch |
| 6,765,036 B2 | 7/2004 | Dede |
| 6,767,955 B2 | 7/2004 | Jia |
| 6,852,795 B2 | 2/2005 | Bissinger |
| 6,852,822 B1 | 2/2005 | Bissinger |
| 6,899,948 B2 | 5/2005 | Zhang |
| 6,933,327 B2 | 8/2005 | Yamakawa |
| 7,114,951 B2 | 10/2006 | Sun |
| 7,137,818 B2 | 11/2006 | Savic |
| 7,537,452 B2 * | 5/2009 | Oxman et al. ............ 433/228.1 |
| 7,988,448 B2 | 8/2011 | van der Zel |
| 2003/0152888 A1 | 8/2003 | Sun |
| 2003/0166740 A1 | 9/2003 | Mitra |
| 2003/0195273 A1 | 10/2003 | Mitra |
| 2005/0250868 A1 | 11/2005 | Suzuki |
| 2005/0252413 A1 | 11/2005 | Kangas |
| 2005/0252414 A1 | 11/2005 | Craig |
| 2005/0256223 A1 | 11/2005 | Kolb |
| 2006/0034780 A1 | 2/2006 | Guan |
| 2007/0166450 A1 | 7/2007 | Simonton |
| 2007/0248927 A1 | 10/2007 | Luchterhandt |
| 2007/0287764 A1 * | 12/2007 | Oxman et al. ............... 522/31 |
| 2009/0005469 A1 * | 1/2009 | Craig et al. .................. 522/78 |
| 2009/0075239 A1 | 3/2009 | Abuelyaman |
| 2010/0311858 A1 * | 12/2010 | Holmes et al. ............... 522/47 |
| 2011/0045443 A1 * | 2/2011 | Simonton et al. .......... 433/217.1 |

FOREIGN PATENT DOCUMENTS

| | | |
|---|---|---|
| DE | 10146883 | 4/2003 |
| EP | 0173567 A2 | 3/1986 |
| EP | 0189540 | 8/1986 |
| EP | 0201031 | 11/1986 |
| EP | 0201778 | 11/1986 |
| EP | 0231420 | 8/1987 |
| EP | 0238025 | 9/1987 |
| EP | 0373384 | 6/1990 |
| EP | 0712622 | 5/1996 |
| EP | 1051961 | 11/2000 |
| EP | 1400232 | 3/2004 |
| EP | 1464297 | 10/2004 |
| JP | 2005041825 | 2/2005 |
| WO | WO 94/14792 | 7/1994 |
| WO | WO 96/19471 | 6/1996 |
| WO | WO 00/38619 | 7/2000 |
| WO | WO 00/42092 | 7/2000 |
| WO | WO 01/07444 | 2/2001 |
| WO | WO 01/87240 | 11/2001 |
| WO | WO 01/92271 | 12/2001 |
| WO | WO 03/059295 | 7/2003 |
| WO | WO 03/063804 | 8/2003 |
| WO | WO 2005/051332 | 6/2005 |
| WO | WO 2006/122074 | 11/2006 |
| WO | WO 2006/122081 | 11/2006 |
| WO | WO 2007/041477 | 4/2007 |
| WO | WO 2008/083067 | 7/2008 |
| WO | WO 2009/058854 | 5/2009 |

OTHER PUBLICATIONS

Den Hertog, "The Reactivity of Bromine Atoms in Brominated Pyridines", Recueil Tray. Chim. Pays-Bas, Mar. 1948, vol. 67, pp. 385-392.

Evans, "Free Radical Ring-Opening Polymerization of Cyclic Allylic Sulfides. 2. Effect of Substituents on Seven- and Eight-Membered Ring Low Shrink Monomers," Macromolecules, 2000, vol. 33, No. 18, pp. 6722-6731.

Evans, "Free Radical Ring-Opening Polymerization of Cyclic Allylic Sulfides: Liquid Monomers with Low Polymerization Volume Shrinkage", Journal of Polymer Science: Part A: Polymer Chemistry, 2001, vol., 39, pp. 202-215.

Evans, "Free-Radical Ring-Opening Polymerization of Cyclic Allylic Sulfides", Macromolecules, 1996, vol. 29, No. 22, pp. 6983-6989.

Evans, "New Free-Radical Ring-Opening Acrylate Monomers," Macromolecules, 1994, vol. 27, No. 26, pp. 7935-7937.

Lee, "Handbook of Epoxy Resins", McGraw-Hill Inc., (1967).

MANN, Electrochemical Reactions in Nonaqueous Systems, Marcel Dekker, Inc., (1970).

Matsumoto, "Autofluorescence in human dentine in relation to age, tooth type and temperature measured by nanosecond time-resolved fluorescence microscopy", Arch. Oral. Biol, 1999, vol. 44, pp. 309-318.

Nikas, "The Reaction of Trimethylsilylethynyl(phenyl)iodonium Triflate with Some Phenolates: Formation of Substitution and $sp^2$ C-H Insertion Product", Molecules, 2000, vol. 5, pp. 1182-1186.

Spitzer, "The Total Luminescence of Bovine and Human Dental Enamel", Calcified Tissue Res., 1976, vol. 20, No. 1, pp. 201-208.

Weinberg, ed., "Technique of Electroorganic Synthesis", Techniques of Chemistry, 1975, vol. V, Part II, John Wiley & Sons, Inc.

Wyszecki, "Color Science: Concepts and Methods, Quantitative Data and Formulae", 2nd Edition, John Wiley & Sons, Inc., (1982).

Wyszecki, "Color Science: Concepts and Methods, Quantitative Data and Formulae", 2nd Edition, Wiley Classics Library Edition (2000).

International Search Report of PCT/US2007/088528, pp. 4.

Written Opinion for ISA Application No. PCT/US2007/088528, pp. 5.

International Search Report of PCT/US2008/081573, pp. 3.

Written Opinion for ISA Application No. of PCT/US2008/081573, pp. 5.

* cited by examiner

DENTAL COMPOSITIONS WITH NATURAL TOOTH FLUORESCENCE

CROSS-REFERENCE TO RELATED APPLICATIONS

The present application is the National Stage filing under 35 U.S.C. 371 of International Application No. PCT/US2007/088528 filed Dec. 21, 2007, which claims priority to U.S. Provisional Application Ser. No. 60/877,513, filed on Dec. 28, 2006, the entirety of which is incorporated herein by reference.

TECHNICAL FIELD

The invention generally relates to dental compositions that contain a polycyclic aromatic compound and have fluorescence similar to that of natural teeth.

BACKGROUND

Over the past several decades, there has been an increasing demand among dentists and dental patients for more aesthetic dental restorations. High aesthetic quality is particularly important for easily visible restorations, such as those involving the front teeth, but may also be desirable for restorations involving teeth that are not as readily visible.

The dental industry's growing focus on aesthetic dentistry has led to the development of dental restorative compositions that more closely mimic the appearance of natural teeth. For example, tooth-colored, composite resin materials have been developed that can be used in place of, for example, metal amalgam fillings, to provide more natural looking dental restorations. In recent years, highly aesthetic composite materials, such as 3M ESPE™ FILTEK™ Supreme Plus Universal Restorative (3M Company, St. Paul, Minn.), have become available with shading systems and opacity options that make it possible for a dentist to create dental restorations so natural looking they are virtually undetectable to the casual observer.

Since human teeth fluoresce when irradiated with ultraviolet (UV) light, dental restorations that fail to exhibit fluorescence similar to that of natural teeth may become more noticeable when viewed under UV radiation or "black light" conditions. For example, dental restorative compositions that use resin systems that do not fluoresce as intensely as natural teeth and/or that contain components, such as color stabilizers, that diminish the fluorescence of the composition, may provide restorations that appear darker than surrounding teeth under UV light. Conversely, dental compositions that contain components with greater fluorescence than that of natural teeth may appear brighter than surrounding teeth under these conditions. Consequently, restorations made with such compositions, even if undetectable under normal visible light or full spectrum lighting conditions, may suffer from reduced aesthetic quality when exposed to UV light.

SUMMARY

The invention features hardenable dental compositions and methods that provide dental restorations having natural tooth fluorescence. This allows for the creation of aesthetic dental restorations that keep their natural-looking appearance even when viewed under UV radiation or black light.

The compositions of the invention typically comprise a resin system that includes a polymerizable component combined with an initiator system. The polymerizable component typically comprises at least one ethylenically unsaturated compound, such as a (meth)acrylate, and the initiator system typically comprises one or more electron donors. The compositions also contain a polycyclic aromatic component that serves as a fluorescing dye that, when present in an appropriate amount, provides the composition with fluorescence mimicking that of natural teeth. The exact fluorescence of the compositions will vary depending upon the precise amount and identify of the polycyclic aromatic component present in the composition, but generally ranges from about 25 to about 100 when measured using the test methods described herein.

Suitable compounds for use in the polycyclic aromatic component of the present invention include, but are not limited to, biphenylenes, naphthalenes, anthracenes, benzanthracenes, pyrenes, azulenes, pentacenes, decacyclenes, and derivatives (such as acenaphthenes) and combinations thereof. A particularly suitable group of polycyclic aromatic compounds include anthracene derivatives, including unsubstituted anthracene or anthracene substituted by organic groups including an alkyl, aryl (e.g., phenyl), aryloxy, alkoxy, or combinations thereof. Exemplary alkyl substituted anthracene include 2,6-di-tert-butylanthracene, 9-methylanthracene, or 9,10-dimethylanthracene. Exemplary alkoxy substituted anthracenes include 2-ethyl-9,10-dimethoxyanthracene (EDMOA), 9,10-diethoxyanthracene, 1,4-dimethoxyanthracene, or 9,10-dimethoxyanthracene.

Polycyclic aromatic compounds, such as EDMOA and other anthracene derivatives, are also useful as electron donors in initiator systems for the polymerization of polymerizable dental compositions; however, the amount of polycyclic aromatic compounded needed to provide the dental composition with natural tooth fluorescence is significantly lower than the amount needed to perform the electron donor function. Thus, for dental resin systems that have a primary electron donor that, when compounded with the other components of the system and the system is cured, provides a non-fluorescent or weakly fluorescent material, a hardenable dental composition with natural tooth fluorescence can be obtained by adding a relatively small amount of a polycyclic aromatic component to the uncured formulation.

Accordingly, in some implementations of the invention, the initiator system of the hardenable dental composition comprises a primary electron donor in combination with a polycyclic aromatic component that serves as a secondary electron donor and also provides the composition with natural tooth fluorescence. The primary electron donor is typically present in an amount of at least 0.05 wt-%, more typically at least 0.07 wt-%, of the resin system and comprises a compound that, when used as the only electron donor in the system, would provide a hardened material that is non-fluorescent or weakly fluorescent. The polycyclic aromatic component is generally present in an amount less than about 0.5 wt-%, more typically less than about 0.3 wt-%, and most typically less than about 0.1 wt-% of the resin system. Typically, it is present in a range from about 0.005 wt-% to about 0.05 wt-% of the resin system. The weight percentages of these components in the total composition are from about 20% (for highly filled compositions) to about 60% (for less highly filled compositions) of the values provided above for the resin system.

The dental compositions of the invention may also optionally include a filler system. In some implementations, the filler system includes one or more silane-treated nanofillers, selected from nano silica, nano zirconia, zirconia-silica nanoclusters, and combinations thereof.

In another aspect, the invention provides a method of making of dental composition having natural tooth fluorescence, which method involves the steps of: (a) providing a dental resin system that, when cured, has non-natural tooth fluorescence, (b) adding a sufficient amount of a polycyclic aromatic component to the resin system to provide a composition having a natural tooth fluorescence, and (c) optionally comparing the fluorescence of the composition to the fluorescence of a natural tooth.

The dental compositions of the invention are useful in a variety of dental and orthodontic applications, including as dental restoratives, dental adhesives, dental cements, cavity liners, orthodontic adhesives, dental sealants, dental coatings, and the like. The compositions and related methods may be used to prepare dental articles by hardening to form, for example, dental fillings, dental mill blanks, dental crowns, dental prostheses, orthodontic devices, and the like.

The above summary is not intended to describe each embodiment or every implementation of the invention. Other embodiments, features, and advantages of the present invention will be apparent from the following detailed description thereof, and from the claims.

DEFINITIONS

As used herein, the phrase "natural tooth fluorescence" means that when viewed under ultraviolet light of 365 nm the composition exhibits a fluorescence intensity and wavelength resembling that of a natural tooth. Although the fluorescence of natural teeth varies from subject to subject and the desired closeness of the match of the composition's fluorescence to that of a natural tooth depends on the precise situation and/or aesthetic demands of the patient (e.g., molars and other teeth that are not easily visible may not need to match the natural tooth fluorescence as closely as front teeth). Typically, the compositions of the invention exhibit a fluorescence in the range of about 20 to about 100, more typically from about 30 to about 90, and most typically from about 35 to about 85, when measured using the test methods described herein.

By "non-natural tooth fluorescence" is meant fluorescence that is visibly less intense or more intense than the fluorescence exhibited by natural teeth, or fluoresces at a visibly different wavelength than that of natural teeth. When used in reference to an electron donor component (e.g. "an electron donor with non-natural tooth fluorescence," etc.), the term means that when the electron donor is compounded with the other components of the composition and the composition is subsequently cured, its fluorescence is visibly different in intensity or wavelength than that of natural teeth. Thus, an electron donor, such as ethyl (4-dimethyl amino) benzoate (EDMAB), that is strongly fluorescent when viewed under black light in its pure form may nevertheless be considered to have "non-natural tooth fluorescence" if the electron donor when compounded and cured exhibits a fluorescence in the cured material that is visibly less intense or otherwise different from that of natural teeth.

By "non-fluorescent" is meant that when irradiated with UV radiation, the compound, composition, or material exhibits no visible fluorescence or is only weakly fluorescent, i.e. substantially below the fluorescence exhibited by a natural human tooth such that the difference is easily visible. When used in reference to an electron donor component (e.g. "a non-fluorescent electron donor," etc.), the term means that when the electron donor is compounded with the other components of the composition and the composition is subsequently cured, it does not exhibit any visible fluorescence or is weakly fluorescent. Thus, an electron donor, such as ethyl (4-dimethyl amino) benzoate (EDMAB), that is strongly fluorescent when viewed under black light in its pure form may nevertheless be considered to be "non-fluorescent" if the electron donor when compounded and cured no longer exhibits a strongly fluorescent character in the cured material.

By "polycyclic aromatic component" is meant at least one polycyclic organic compound having two or more fused aromatic rings, including their alkyl-, alkoxy-, aryl-, and aryloxy-substituted derivatives. By "fused" is meant two aromatic rings with a shared side or with opposing sides directly joined by carbon-carbon bonds.

By "electron donor" is meant a compound that has a substituent or moiety that can donate electrons. Suitable examples include, but are not limited to, a primary amino, secondary amino, tertiary amino, hydroxy, alkoxy, aryloxy, alkyl, or combinations thereof.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking.

By "dental composition" is meant an unfilled or filled (e.g. a composite) material (e.g., a dental or orthodontic material) that are capable of being applied or adhered to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure.

By "hardenable dental composition" is meant a dental composition, such as a paste, that can be hardened to form a dental article.

By "dental article" is meant an article that can be adhered (e.g., bonded) to an oral surface (e.g., a tooth structure). Typically, the dental article is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge structures, abutments, orthodontic appliances and devices, and prostheses (e.g., partial or full dentures).

As used herein, the terms "dental composition" and "dental article" are not limited to compositions and articles used in dental applications, but also include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like), respectively.

By "oral surface" is meant a soft or hard surface in the oral environment. Hard surfaces typically include tooth structure including, for example, natural and artificial tooth surfaces, bone, tooth models, dentin, enamel, cementum, and the like By "filler" is meant a particulate material suitable for use in the oral environment. Dental fillers generally have an average particle size of at most 100 micrometers.

By "nanofiller" is meant a filler having an average primary particle size of at most 200 nanometers. The nanofiller component may be a single nanofiller or a combination of nanofillers. Typically the nanofiller comprises non-pyrogenic nanoparticles or nanoclusters. By "nanostructured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" is synonymous with "nano-sized particles," and refers to particles having an average size of at most 200 nanometers. As used herein for a spherical particle, "size" refers to the diameter of the particle. As used herein for a non-spherical particle, "size" refers to the longest dimension of the particle. In certain embodiments, the nanoparticles are comprises of discrete, non-aggregated and non-agglomerate particles.

By "nanocluster" is meant an association of nanoparticles drawn together by relatively weak intermolecular forces that cause them to clump together, i.e. to aggregate. Typically, nanoclusters have an average size of at most 10 micrometers.

As used herein, the term "ethylenically unsaturated compound" is meant to include monomers, oligomers, and polymers having at least one ethylenic unsaturation.

By "polymerization" is meant the forming of a higher weight material from monomer or oligomers. The polymerization reaction also can involve a cross-linking reaction.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

The terms "comprises", "comprising" and variations thereof do not have a limiting meaning where these terms appear in the description and claims.

The recitation herein of numerical ranges by endpoints is intended to include all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION

The present invention features the use of a polycyclic aromatic component as a fluorescing dye for providing dental compositions and materials with fluorescence mimicking that of natural teeth. Natural tooth fluorescence is particularly desirable for resin/filler composite materials used in restorative dentistry where the aesthetic quality of the material is often important. Such compositions typically include a polymerizable component, an initiator system, one or more fillers and/or other additives depending on the desired application. Polycyclic aromatic compounds are advantageous as fluorescing dyes in these compositions because they can be used in relatively low concentrations due to their strong fluorescence, and generally do not affect the opacity of dental composites. In addition, certain polycyclic aromatics, such as 2-ethyl 9,10-dimethoxy anthracene (EDMOA), can be used as a secondary electron donor in the photo initiator system of the dental resin thus allowing for a reduction in the amount of the primary electron donor need for effective polymerization of the composition.

Polymerizable Component

The dental compositions of the present invention are hardenable, typically due the presence of a polymerizable component. In some embodiments, the compositions can be hardened (e.g., polymerized by conventional photopolymerization and/or chemical polymerization techniques) prior to applying it to an oral surface. In other embodiments, the compositions can be hardened (e.g., polymerized by conventional photopolymerization and/or chemical polymerization techniques) after it has been applied to an oral surface.

In certain embodiments, the compositions are photopolymerizable, i.e., the compositions contain a photoinitiator system that upon irradiation with actinic radiation initiates the polymerization (or hardening) of the composition. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions.

The polymerizable component typically includes one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof.

The compositions, especially in photopolymerizable implementations, may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments, the polymerizable component includes PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and/or NPGDMA (neopentylglycol dimethacrylate). Various combinations of these hardenable components can be used if desired.

When the composition contains an ethylenically unsaturated compound without acid functionality, it is generally present in an amount of at least 5% by weight, more typically at least 10% by weight, and most typically at least 15% by weight ethylenically unsaturated compounds without acid functionality, based on the total weight of the unfilled composition. The compositions of the present invention typically include at most 95% by weight, more typically at most 90% by weight, and most typically at most 80% by weight ethylenically unsaturated compounds without acid functionality, based on the total weight of the unfilled composition.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. Nos. 4,872,936 (Engelbrecht) and 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. Nos. 4,259,075 (Yamauchi et al.), 4,499,251 (Omura et al.), 4,537, 940 (Omura et al.), 4,539,382 (Omura et al.), 5,530,038 (Yamamoto et al.), 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658 (Luchterhandt et al.), filed on Aug. 11, 2004. The compositions may also include a mixture of ethylenically unsaturated compounds both with and without acid functionality.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present invention typically include at most 80% by weight, more typically at most 70% by weight, and most typically at most 60% by weight ethylenically unsaturated compounds with acid functionality, based on the total weight of the unfilled composition.

Initiator System

In certain embodiments, the compositions of the present invention are photopolymerizable, i.e., the compositions contain a photopolymerizable component and a photoinitiator system that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. Nos. 4,298,738 (Lechtken et al.), 4,324,744 (Lechtken et al.), 4,385,109 (Lechtken et al.), 4,710,523 (Lechtken et al.), and 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions.

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight (including water) of the components of the composition. Typically, the reducing agent is present in an amount of no greater than 10% by weight, and more typically no greater than 5% by weight, based on the total weight (including water) of the components of the composition.

Typically, the oxidizing agent, if used at all, is present in an amount of at least 0.01% by weight, and more typically at least 0.10% by weight, based on the total weight (including water) of the components of the composition. Typically, the oxidizing agent is present in an amount of no greater than 10% by weight, and more typically no greater than 5% by weight, based on the total weight (including water) of the components of the composition.

The reducing or oxidizing agents can be microencapsulated as described in U.S. Pat. No. 5,154,762 (Mitra et al.). This will generally enhance shelf stability of the composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, including photoinitiator systems or with a composition such as described U.S. Pat. No. 5,154,762 (Mitra et al.).

Polycyclic Aromatic Component

The compositions of the invention include at least one polycyclic aromatic component, which serves as a fluorescing dye to provide the composition, and/or a hardened product or material (e.g. a dental restoration) made from the composition, with natural tooth fluorescence. The polycyclic aromatic compounds may also optionally act as an additional electron donor in the initiator system of the composition.

The polycyclic aromatic component may comprise one or more polycyclic aromatic compounds (i.e., polycyclic compounds having two or more fused or joined aromatic rings), including their alkyl- and aryl-substituted derivatives. By "fused" is meant two aromatic rings with a shared side or with opposing sides directly joined by carbon-carbon bonds.

Representative classes of useful polycyclic aromatic compounds include, but are not limited to, biphenylenes, naphthalenes, anthracenes, benzanthracenes, pyrenes, azulenes, pentacenes, decacyclenes, and derivatives (such as acenaphthenes) and combinations thereof. Typically useful polycyclic aromatic compounds include 1,4-dimethoxyanthracene, 9-methylanthracene, 9,10-methylanthracene, anthracene, biphenylene, and combinations thereof.

More specifically, polycyclic aromatic compounds conforming to the structures shown below may be employed.

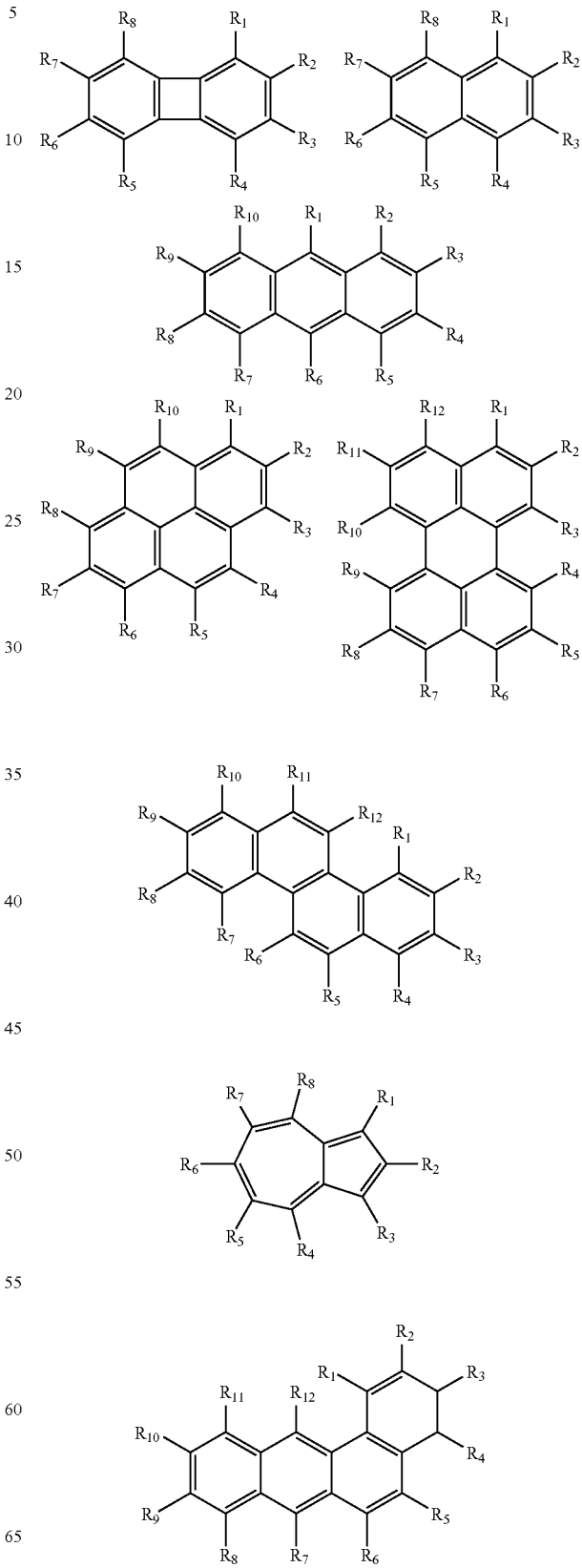

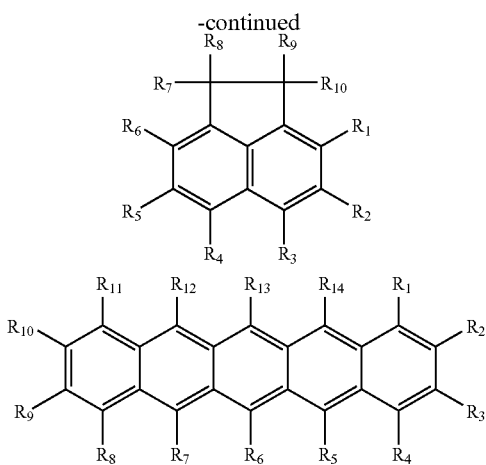

In the foregoing structures, the substituents $R_1$ to $R_{14}$ may be any group that does not have a substantially adverse effect on polymerization, and typically are independently selected from H or hydrocarbon groups. The hydrocarbon groups may be alkyl groups (e.g., $C_{1-10}$ alkyl, $C_{2-10}$ alkenyl, or $C_{3-10}$ cycloalkyl groups) or aromatic groups (e.g., $C_{5-10}$ aromatic groups). The hydrocarbon groups can be optionally substituted by one or more halogen, —CN, —OH, —SH, —COOH, —COOC$_{1-10}$ alkyl, —(C$_{1-10}$ alkyl)$_{0-1}$-COH, —(C$_{1-10}$ alkyl)$_{0-1}$-CO—C$_{1-10}$ alkyl, —CO—C$_{1-10}$ alkyl, as well as other hydrocarbon groups. The various R-group substituents may also cooperate to form an aromatic or cycloalkyl ring. Typical R-group substituents are methyl, ethyl, methoxy, and ethoxy.

Suitable polycyclic aromatic electron donor compounds include: biphenylene, anthracene, 9-methylanthracene, 9-vinyl anthracene, 9-phenylanthracene, 9,10-diphenylanthracene, 9,10-dimethylanthracene, 2-ethylanthracene, acenaphthene, pyrene, pentacene, decacyclene, azulene, 7,12-dimethyl-1,2-benzanthracene, 1,2-benzanthracene, 1,4-dimethylnaphthalene, 2,3,5-trimethylnaphthalene, and combinations thereof. All of these compounds are available from Sigma-Aldrich, St. Louis, Mo.

Suitable polycyclic aromatic compounds include anthracene derivatives. More specifically, anthracene-based electron donor compounds conforming to the structure I shown below may be employed.

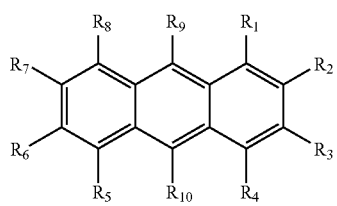

In the above structure I, the substituents $R_1$ to $R_{10}$ may be any group that does not have a substantially adverse effect on acidic polymerization, and are independently selected from H, alkyl groups, aryl groups and/or alkoxy groups, preferably $C_1$-$C_{10}$ alkyl and/or $C_1$-$C_{10}$ alkoxy. Typical R-group substituents are methyl, ethyl, propyl, butyl, tert-butyl, methoxy, and ethoxy.

Particularly useful anthracene-based compounds include: 2-ethyl-9,10-dimethoxyanthracene (EDMOA), 9,10-dimethylanthracene, 9,10-diethoxyanthracene, 1,4-dimethoxyanthracene, 9-methylanthracene, 2-ethylanthracene, 2-tert-butylanthracene, 2,6-di-tert-butylanthracene, 9,10-diphenyl-2,6-di-tert-butylanthracene, and combinations thereof. All of these compounds with the exception of the 2,6-di-tert-butylanthracene derivatives are available from Sigma-Aldrich, St. Louis, Mo. The anthracene-based compounds for use in the invention, especially when used both as a fluorescing dye and an additional electron donor, may possess one or more (and more typically several if not all) of the following properties: (a) they are soluble or partially soluble in the polymerizable composition; (b) they do not absorb a significant amount of light at the wavelength of the light used to photopolymerize the composition, typically the wavelength at which the visible light sensitizer exhibits maximum absorption, by which it is meant that the polycyclic aromatic compound does not detrimentally affect the performance of the visible light sensitizer; (c) they have an oxidation potential ($E_{ox}$) greater than 0 but less than that of 1,4-dimethoxybenzene when measured versus a saturated calomel electrode (SCE); (d) a $pk_b$ greater than about 8; (e) they impart not more than a minimal amount of objectionable color to the composition; and (f) they cause no more than a minimal amount of polymerization inhibition. Other factors that may influence the selection of the anthracene-based compound for a particular composition include the polymerizable component and other components of the initiator system (e.g., the iodonium salt, and the visible light sensitizer) that have been chosen, as well as the shelf stability of the polymerizable composition.

While suitable anthracene-based compounds for use as an additional electron donor typically have an $E_{ox}$ greater than zero and less than or equal to that of 1,4-dimethoxybenzene, it is more suitable that the anthracene-based compound have an $E_{ox}$ that is less than about 1.35 volts when measured using a saturated calomel electrode (SCE), and even more suitable that the $E_{ox}$ be between about 0.5 and 1.34 volts (vs. a SCE). $E_{ox}$ values can be measured experimentally, or obtained from established reference sources, such as N. L. Weinburg, Ed., *Technique of Electroorganic Synthesis Part II Techniques of Chemistry*, Vol. V (1975), and C. K. Mann and K. K. Barnes, *Electrochemical Reactions in Nonaqueous Systems* (1970).

The polycyclic aromatic compound or compounds (e.g. an anthracene derivative or a biphenylene) are typically present at about 0.0005 to about 0.01 weight percent, more typically about 0.0005 to about 0.008 weight percent, and most typically about 0.0005 to about 0.007 weight percent, based on the overall composition.

Filler(s)

The compositions of the present invention may optionally contain one or more fillers. Fillers may be selected from one or more of a wide variety of materials suitable for incorporation in compositions used for dental applications, such as fillers currently used in dental restorative compositions, and the like.

The choice of the filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926 B1.

The amount of filler that is incorporated into the composite, referred to herein as the "loading level" and expressed as a weight percent based on the total weight of the dental material, will vary depending on the type of filler, the curable resin and other components of the composition, and the end use of the composite.

For some dental materials, such as sealants, the compositions of the invention can be lightly filled (e.g., having a loading level of less than about 40 weight percent) or unfilled. In such implementations, the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level is generally at least 40 weight percent, and more typically is between about 60 and 90 weight percent.

The filler(s) used in the compositions of the invention is typically finely divided. The filler(s) can have a unimodial or polymodial (e.g., bimodal) particle size distribution. The maximum particle size (the largest dimension of a particle, generally, the diameter) of the filler(s) is typically less than 20 micrometers, more typically less than 10 micrometers, and most typically less than 5 micrometers. The average particle size of the filler(s) is typically less than 0.1 micrometers, and more typically less than 0.075 micrometer.

The filler(s) may be an inorganic material. It may also be a crosslinked organic material that is insoluble in the resin system, and is optionally filled with inorganic filler. The filler(s) should in any event be nontoxic and suitable for use in the mouth. The filler(s) can be radiopaque or radiolucent. The filler typically is substantially insoluble in water.

Examples of suitable inorganic fillers are naturally occurring or synthetic materials including, but not limited to: quartz (i.e. silica, $SiO_2$); nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). In some embodiments, the silica or nanosilica particles are non-pyrogenic, i.e. comprise non-fumed silica. Examples of suitable organic filler particles include filled or unfilled pulverized olycarbonates, polyepoxides, and the like.

The filler may be acid-reactive, non-acid-reactive, or a combination thereof. Suitable non-acid-reactive filler particles include quartz, submicron silica, nano silica, nano zirconia, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments. In some implementations of the invention, the filler system may contain a combination of at least one filler comprising heavy metal oxide nanoparticles (e.g., zirconia nanoparticles), and/or at least one filler comprising non-heavy metal oxide particles (e.g. silica nanoparticles), and/or at least filler comprising a heavy metal oxide and a non-heavy metal oxide (e.g. clusters of zirconia and silica nanoparticles).

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

In some implementations, the composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass, if present, typically contains sufficient elutable cations so that a hardened dental composition will form when the glass is mixed with the components of the hardenable composition. The glass also typically contains sufficient elutable fluoride ions so that the hardened composition will have cariostatic properties. Such glass can be made from a melt containing fluoride, alumina, and other glass-forming ingredients using techniques familiar to those skilled in the FAS glassmaking art. The FAS glass, if present, is typically in the form of particles that are sufficiently finely divided so that they can conveniently be mixed with the other cement components and will perform well when the resulting mixture is used in the mouth.

Generally, the average particle size (typically, diameter) for FAS glass used in such compositions is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEM-FIL Superior (Dentsply International, York, Pa.). Mixtures of fillers can be used if desired.

The surface of the filler particles can also be treated with a coupling agent in order to enhance the bond between the filler and the resin. Suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$-$SiO_2$) fillers and nanofillers, silane-treated silica fillers and nanofillers, silane-treated zirconia fillers and nanofillers, and combinations thereof are especially suitable for certain restorative compositions.

Other suitable fillers are disclosed in U.S. Pat. Nos. 6,387,981 (Zhang et al.); 6,572,693 (Wu et al.); 6,730,156 (Windisch); and 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For some embodiments of the present invention that include filler (e.g., dental adhesive compositions), the compositions typically include at least 1% by weight, more typically at least 2% by weight, and most typically at least 5% by weight filler, based on the total weight of the composition. For such embodiments, compositions of the present invention typically include at most 40% by weight, more typically at most 20% by weight, and most typically at most 15% by weight filler, based on the total weight of the composition.

For other embodiments (e.g., wherein the composition is a dental restorative or an orthodontic adhesive), compositions of the present invention typically include at least 40% by weight, more typically at least 45% by weight, and most typically at least 50% by weight filler, based on the total weight of the composition. For such embodiments, compositions of the present invention typically include at most 90% by weight, more typically at most 80% by weight, even more typically at most 70% by weight filler, and most typically at most 50% by weight filler, based on the total weight of the composition.

Other Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof.

In some implementations of the invention, the compositions are non-aqueous. In other implementation, the compositions may optionally contain water. The water can be distilled, deionized, or plain tap water. If present, the amount of water should be sufficient to provide adequate handling and mixing properties and/or to permit the transport of ions, particularly in a filler-acid reaction. In such embodiments, water represents at least about 1 wt-%, and more preferably at least about 5 wt-%, of the total weight of ingredients used to form the hardenable composition. Generally, water represents no greater than about 75 wt-%, and more preferably no greater than about 50 wt-%, of the total weight of ingredients used to form the hardenable composition.

If desired, the compositions of the invention may contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of the Compositions

The dental compositions of the present invention can be prepared by combining all the various components using conventional mixing techniques. The resulting composition may optionally contain fillers, solvents, water, and other additives as described herein. Typically, photopolymerizable compositions of the invention are prepared by simply admixing, under "safe light" conditions, the components of the inventive compositions. Suitable inert solvents may be employed if desired when affecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the polymerizable resin, with or without the use of mild heating to facilitate dissolution.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on previous experience with dental materials. When the dental material is applied to a tooth, the tooth can optionally be pre-treated with a primer and/or an adhesive by methods known to those skilled in the art.

The compositions can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation. Also, for those implementation in which the dental composition is a resin-modified glass ionomer (RMGI), the polyacid, acid-reactive filler and water generally would not all be present in the same part, although any two of these may be grouped together in the same part along with any combination of other components.

The components of the composition can be included in a kit, where the contents of the composition are packaged to allow for storage of the components until they are needed.

The components of the composition can be mixed and clinically applied using conventional techniques. A curing light is generally required for the initiation of photopolymerizable compositions. The compositions may be in the form of composites or restoratives that adhere very well to dentin and/or enamel. Optionally, a primer layer can be used on the tooth tissue on which the hardenable composition is used.

The invention encompasses a wide variety of dental compositions, which may be filled or unfilled. Exemplary dental materials include dental restoratives (e.g., composites, fillings, sealants, inlays, onlays, crowns, and bridges), orthodontic appliances, and orthodontic adhesives. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth.

The features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Unless otherwise noted, reagents and solvents were obtained from Sigma-Aldrich Corp., St. Louis, Mo.

As used herein,

"bisGMA" refers to 2,2-bis[4-(2-hydroxy-3-methacryloyloxypropoxy)phenyl]propane;

"TEGDMA" refers to triethyleneglycol dimethacrylate, obtained from Sartomer Co., Inc., Exton, Pa.;

"UDMA" refers to diurethane dimethacrylate, obtained under the trade designation "ROHAMERE 6661-0" from Rohm America LLC, Piscataway, N.J.;

"BisEMA6" refers to ethoxylated bisphenol A dimethacrylate, obtained from Sartomer Co., Inc., Exton, Pa.;

"BHT" refers to butylated hydroxytoluene;

"Zr—Si FILLER" refers to silane-treated zirconia-silica nanocluster filler prepared essentially as described in U.S. Pat. No. 6,730,156;

"SILICA FILLER" refers to a silane-treated nano-sized silica having a nominal particle size of approximately 20 nanometers, prepared essentially as described for FILLER F in U.S. Patent Publication No. 2005/0252413;

"ZIRCONIA FILLER" refers to silane-treated nano-sized zirconia prepared essentially as described in Preparatory Example 1A in U.S. Patent Publication No. 2005/0252413;

"CPQ" refers to camphorquinone;

"EDMAB" refers to ethyl 4-dimethylaminobenzoate;

"EDMOA" refers to 2-ethyl-9,10-dimethoxyanthracene;

"DPIPF6" refers to diphenyliodonium hexafluorophosphate, obtained from Alfa Aesar, Ward Hill, Mass.;

"TINUVIN" refers to a polymerizable UV stabilizer obtained under the trade designation TINUVIN R 796 from Ciba Specialty Chemicals, Tarrytown, N.Y.;

Example 1

A polymerizable resin mixture was prepared by combining the components listed in Table 1 using a Model DAC 150 FVZ SpeedMixer (manufactured by FlackTek, Inc., Landrum, S.C.) at 3000 rpm in three separate one-minute mixing cycles. The weight percentages given in Table 1 are the weight percentages of the components in the resin mixture. Sufficient EDMOA was then combined with the resin mixture to provide a resin mixture containing 0.02 weight percent EDMOA. To this EDMOA-containing polymerizable resin mixture were then added zirconia filler, silica filler, and Zr—Si filler to provide a hardenable dental composition containing 78.5 weight percent filler mixture, the filler mixture having a composition of 90.5 weight percent Zr—Si filler, and 9.5 weight percent of a mixture of 27 weight percent zirconia filler and 73 weight percent silica filler. This hardenable dental composition contained 0.0043 weight percent EDMOA. A disk of this composition having a thickness of one millimeter and a diameter of thirty millimeters was prepared and cured for two minutes in a hydraulic press (obtained from Carver, Inc., Wabash, Ind.) at 68.95 MPa (10,000 pounds per square inch) pressure. The press had been fitted with fiber optic cables to direct light to the disk from a Model A20500 ACE light source (Schott North America, Inc., Auburn, N.Y.). The disk was removed from the press and was further cured for 90 seconds using a stroboscopic light curing device (UNISX; Heaeus Kulzer, Inc., Armonk, N.Y.). The fluorescence of this cured disk was evaluated using a color viewing booth (obtained under the trade designation SPECTRALIGHT, from Gretag-Macbeth LLC, New Windsor, N.Y.) with an ultraviolet light source. After the cured disk was placed in the color viewing booth and was illuminated with ultraviolet light, it was photographed using a digital camera (obtained under the trade designation REBEL XT, Canon U.S.A., Inc., Lake Success, N.Y.) that had been calibrated (white balance) using a sheet of non-fluorescent white cardboard under black light. Greyscale photographs taken under these conditions were considered to approximate the appearance of the compositions to the unaided human eye. The fluorescence of this cured disk was found to be essentially the same as that of natural human teeth.

TABLE 1

Composition of Polymerizable Resin Mixture of Example 1.

| Component | Weight Percentage in Resin |
| --- | --- |
| bisGMA | 24.20 |
| UDMA | 33.88 |
| bisEMA6 | 33.88 |
| TEGDMA | 4.84 |
| CPQ | 0.16 |
| DPIHFP | 0.48 |
| EDMAB | 0.97 |
| BHT | 0.15 |
| TINUVIN | 1.45 |

Example 2

The polymerizable resin mixture of Example 2 was prepared essentially as described in Example 1, except that the composition was pigmented to the A3 shade. A disk of this resin mixture was prepared and cured essentially as described in Example 1. A HunterLab Model UltraScan SE spectrophotometer (manufactured by Hunter Associates Laboratory, Inc., Reston, Va.) was used to determine the fluorescence emission (referred to herein as the fluorescence) of the cured disk over two wavelength ranges, 420 nm to 520 nm, and 420 nm to 570 nm. Two sets of emission data were collected for each wavelength range, the first set with the disk illuminated with unfiltered light from a D65 lamp, and the second set with the disk illuminated with the light from a D65 lamp that was first passed through a 420 nm cutoff filter. For each wavelength range, the emission data that was collected using the 420 nm cutoff filter was subtracted from the emission data that was collected using unfiltered light, to afford data corresponding to fluorescence emission. The wavelength at maximum intensity was found to be 450 nm. A plot of the intensity of the fluorescence emission as a function of wavelength (for each of the two wavelength ranges) afforded fluorescence emission spectra. The integrated area under the curve in each spectrum was estimated using the composite midpoint rule with calculations made by averaging the emission intensity in ten nanometer-wide increments over the wavelength range. Over the wavelength range 420 nm to 520 nm, the fluorescence was found to be 51.2. Over the wavelength range 420 nm to 570 nm, the fluorescence was found to be 21.0.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety as if each were individually incorporated.

What is claimed is:

1. A hardenable dental composition comprising a polycyclic aromatic component, wherein the composition upon hardening has natural tooth fluorescence, and wherein the polycyclic aromatic component is present in an amount less than 0.01 wt-% of the composition.

2. The composition of claim 1, wherein the fluorescence of the composition upon hardening is in a range from about 25 to about 100.

3. The composition of claim 1, wherein the polycyclic aromatic component comprises a substituted anthracene.

4. The composition of claim 3, wherein the substituted anthracene is 2-ethyl 9,10-dimethoxy antracene (EDMOA).

5. A hardenable dental composition comprising a resin system and a filler system, wherein the resin system comprises:
   (a) a polymerizable component and
   (b) an initiator system comprising
      i. an primary electron donor component present in an amount of at least 0.5 wt-% of the resin system; and
      ii. a polycyclic aromatic component that is present in amount less than 0.5 wt-% of the resin system,
   wherein the polycyclic aromatic component is present in an amount less than 0.01 wt-% in the hardenable dental composition.

6. The composition of claim 5, wherein the primary electron donor component comprises an electron donor that provides non-natural tooth fluorescence.

7. The composition of claim 5, wherein the primary electron donor component comprises a non-fluorescent electron donor.

8. The composition of claim 5, wherein the primary electron donor component comprises ethyl (4-dimethyl amino) benzoate (EDMAB).

9. The composition of claim 5, wherein the polymerizable component comprises an ethylentically unsaturated compound.

10. The composition of claim 5, wherein the polycyclic aromatic component comprises a substituted antracene.

11. The composition of claim 10, wherein the substituted anthracene is 2-ethyl 9,10-dimethoxy anthracene (EDMOA).

12. The composition of claim 5, wherein the polycyclic aromatic component is present in an amount from about 0.005 to about 0.05 wt-% of the resin system.

13. A method of making of dental composition having natural tooth fluorescence, the method comprising the steps of:
   (a) providing a dental resin system that, upon curing, provides a material that has a non-natural tooth fluorescence; and
   (b) adding a sufficient amount of a polycyclic aromatic component to the resin system to provide a composition that, upon curing, has a natural tooth fluorescence, wherein the polycyclic aromatic component is present in an amount less than 0.01 wt-% of the dental composition.

14. The method of claim 13, further comprising the step of:
   (c) comparing the fluorescence of the composition to the fluorescence of a natural tooth.

15. The method of claim 13, wherein the resin system comprises an ethylenically unsaturated component.

16. The method of claim 13, wherein the polycyclic aromatic component is a substituted anthracene.

17. The method of claim 16, wherein the substituted anthracene is 2-ethyl 9,10-dimethoxy anthracene (EDMOA).

18. The method of claim 13, wherein the polycyclic aromatic component is present in an amount between 0.005 and about 0.05 wt-% of the resin system.

19. A dental product made by hardening the composition of claim 1.

* * * * *

UNITED STATES PATENT AND TRADEMARK OFFICE
CERTIFICATE OF CORRECTION

PATENT NO. : 8,263,681 B2
APPLICATION NO. : 12/520402
DATED : September 11, 2012
INVENTOR(S) : Bradley Dene Craig It is certified that error appears in the above-identified patent and that said Letters Patent is hereby corrected as shown below:

Column 4
Line 55, delete "like" and insert in place thereof -- like. --

Column 6
Line 67, delete "hexacrylate," and insert in place thereof -- hexaacrylate, --

Column 7
Line 3, delete "bisphenolA" and insert in place thereof -- bisphenol A --

Column 14
Line 34, delete "$E_{ox}$," and insert in place thereof -- $E_{ox}$ --

Line 38, delete "Weinburg," and insert in place thereof -- Weinberg, --

Column 15
Lines 27-28, delete "unimodial or polymodial" and insert in place thereof -- unimodal or polymodal --

Lines 54-55, delete "olycarbonates," and insert in place thereof -- polycarbonates --

Column 20
Line 20 (approx.), delete "Heaeus" and insert in place thereof -- Heraeus --

Column 21
Line 37, in claim 4, delete "antracene" and insert in place thereof -- anthracene --

Signed and Sealed this
Twelfth Day of February, 2013

Teresa Stanek Rea
*Acting Director of the United States Patent and Trademark Office*

Column 22

Line 11 (approx.), in claim 9, delete "ethylentically" and insert in place thereof -- ethylenically --

Line 15 (approx.), in claim 10, delete "antracene." and insert in place thereof -- anthracene. --

Line 39 (approx.), in claim 16, delete "antracene." and insert in place thereof -- anthracene. --